United States Patent [19]

Schad

[11] Patent Number: 4,976,723
[45] Date of Patent: Dec. 11, 1990

[54] SPECIMEN EXCISION FORCEPS

[76] Inventor: Karl Schad, Haupstrasse 28, 7201 Kolbingen, Fed. Rep. of Germany

[21] Appl. No.: 384,708

[22] Filed: Jul. 25, 1989

[30] Foreign Application Priority Data

Jul. 27, 1988 [DE] Fed. Rep. of Germany ....... 8809501

[51] Int. Cl.⁵ .............................................. A61B 17/32
[52] U.S. Cl. .................................... 606/170; 128/751; 606/207
[58] Field of Search ................ 606/83, 167, 168, 170, 606/205, 198, 206, 207; 604/22; 128/749–751, 3, 4, 6; 294/100, 116

[56] References Cited

U.S. PATENT DOCUMENTS

| | | | |
|---|---|---|---|
| 686,578 | 11/1901 | Bowersox | 606/127 |
| 1,742,767 | 1/1930 | Hughes | 294/116 |
| 2,193,073 | 3/1940 | Norton | 294/100 |
| 4,655,219 | 4/1987 | Petruzzi | 606/206 |

FOREIGN PATENT DOCUMENTS 487316 11/1953 Italy .................................. 606/124

OTHER PUBLICATIONS

Ser. vol. 106, c.12.3p4.p1.2. 88196, May 18, 1868, Sondes, Par M. Baujin.

Primary Examiner—C. Fred Rosenbaum
Assistant Examiner—William W. Lewis
Attorney, Agent, or Firm—Walter C. Farley

[57] ABSTRACT

The invention concerns a surgical instrument, in particular an endoscopic specimen excision forceps wherein the forceps mouth (3) is formed by two or more forceps legs (1, 2). The forceps legs are joined together at a pivot (4). On the other side of the pin (4), a traction cable (6) pullbar or the like is linked to the forceps legs. A guide element is connected to the traction cable (6) and has at least one guide groove (8, 9, 14, 16) entered by a lever arm (10, 11, 15) integral with a forceps leg (1, 2, 13) on the other side of the axis of the pivot (4).

11 Claims, 5 Drawing Sheets

FIG. 1.
FIG. 2.
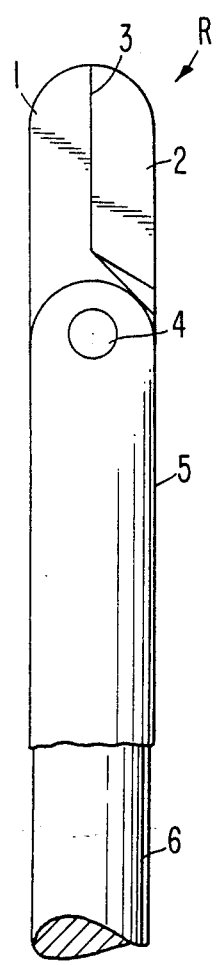
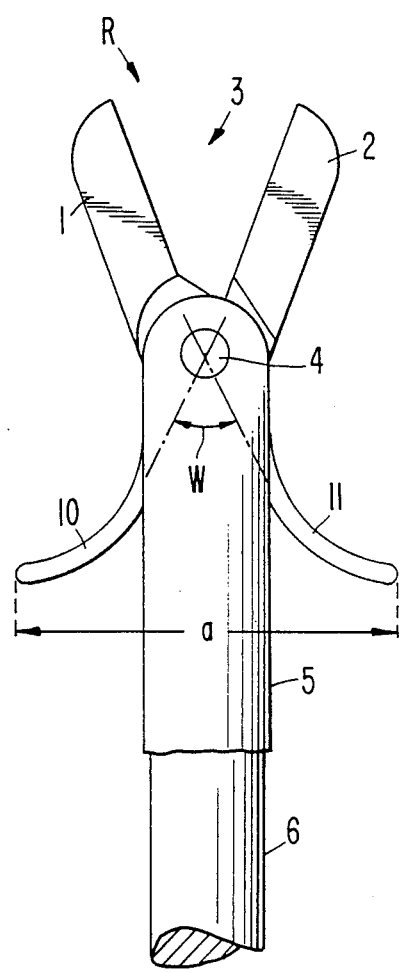

SPECIMEN EXCISION FORCEPS

SPECIFICATION

The invention concerns a surgical instrument, in particular a specimen excision forceps for endoscopy, with a forceps mouth formed by two forceps legs which are connected together by a pivot pin in turn connected to a traction cable, pullbar or the like.

BACKGROUND OF THE INVENTION

Surgical instruments of the general type to which the invention relates are offered commercially in many forms. The forceps mouth formed by the two forceps legs most of the time is linked to a tube and inserted into the human body in order, for instance, to remove tissue samples from specific sites.

This instrument also allows removing entire tissue parts. Again, to some extent, some treatment is made possible at various otherwise inaccessible parts of the human body.

Such a surgical instrument, however, raises the problem that, as a rule, the traction cable is linked by scissor-like lever elements to the two forceps legs. These scissor elements then are straightened out when pulling on the traction cable, so that basically at the end of the closure process, the traction element exerts only a minimal force. Moreover, the levers are comparatively short, and again this reduces the force of cutting. Moreover, the individual scissor elements are connected by suitable rivets or link means to each other and to the forceps legs, and those link means represent substantial weak spots in the overall surgical instrument.

SUMMARY OF THE INVENTION

The object of the invention is to create a surgical instrument of the above kind lacking any weak points from corresponding rivets or link means and allowing the application of increased cutting force to the two forceps legs.

The object is achieved by connecting a guide element to the traction cable or the like and comprises at least one guide groove or channel engaged by at least one lever arm or extension; the two lever arms however will not cross over, but instead subtend an angle between them.

Thereby the corresponding rivets or hinge members for the connection between the guide element and the lever extension are eliminated and hence this weak point is removed as one benefit Another benefit is that each guide channel is oblique, i.e, at an angle to the longitudinal axis of the guide element Thus, each of the lever arms can slide in its associated guide channel such that, when force is applied to the guide element, causing the force applied to the corresponding forceps leg for cutting and gripping is at least the same near the end of the guide element motion and, in some cases, can even be increased.

Preferably one lever arm is integrated into each forceps leg, and these lever arms cross one another and subtend an angle. Thereby, when traction is exerted on the guide element, it is possible to close the forceps mouth. In the closed position the two lever arms disappear into the guide element or into the guide duct or channel, whereas they leave the corresponding guide ducts when the forceps legs are opened.

Another illustrative embodiment of the invention provides for one lever arm being integrated into each forceps leg, but in this case the two lever arms do not cross while subtending an angle between them. In this case, when the ends of the two lever arms are guided toward each other, that is, when the guide element is pulled away from the pivot axis, then the forceps mouth opens.

It should be borne in mind that the shapes of the guide channels and of the lever arms match so that in particular the guide channels leave enough space for displacing the lever arms. No limit is implied hereby on expert know-how As a rule the guide channels are mutually offset both as regards width and height of the guide element, and they diverge toward the outside.

Illustratively, each guide channel may be essentially linear and the corresponding lever arm is then also linear, approximately. Thereby, the cutting force is essentially constant when the guide element is being pulled.

In another embodiment, the particular guide channel is curved and therefore the corresponding lever extension shall be matched in shape. As a result, at the end of cutting, the cutting force shall be increased even more. In each case however the spacing between the two ends of the two lever arms is reduced when pulling on the guide element.

It will become apparent that this forceps also may be driven unilaterally, in which event one forceps leg is held stationary.

This merely requires fixing in place one forceps leg and making the other forceps leg rotatable or pivotable relative to it, this other forceps leg then being equipped with a corresponding lever arm to enter a guide groove of the guide element. Again no restriction on the invention is hereby implied.

Futhermore, three or more forceps legs can be displaced if so desired by one common guide element. Depending on the forceps mouth, the forceps legs illustratively also may be wires. Conceivably as well, the forceps mouth may be angled on the side. The present invention is not restricted to the field of endoscopy, but instead is applicable to all uses of surgical instruments having the form of forceps or scissors.

BRIEF DESCRIPTION OF THE DRAWINGS

The description below of preferred embodiments of the invention is shown in relation to the accompanying drawings, wherein FIG. 1 is an enlarged top plan view of a front zone of a specimen excision forceps R with closed forceps mouth;

FIG. 2 is a top plan view of the forceps of FIG. 2, with the mouth open;

DESCRIPTION OF THE PREFERRED EMBODIMENTS

Figure 3:
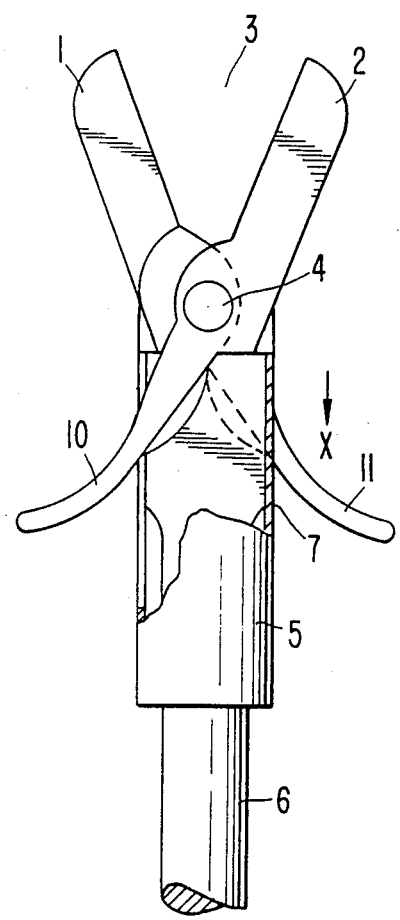
FIG. 3 is a top plan view of the forceps of FIGS. 1 and 2, partly in longitudinal section.

Only the front zone of a specimen excision forceps R is shown in FIGS. 1 through 3 with the forceps mouth 3 formed by the forceps legs 1 and 2. The two forceps legs 1 and 2 are connected in scissor-like manner and pivot about the pivot axis of a common pivot pin 4. The forceps legs 1 and 2 furthermore are connected by this pin 4 to a tube 5 or the like inside of which is guided a slidable traction cable or a pullbar 6.

A guide element 7, also slidable within tube 5, is attached to one end of the traction cable 6. In order to close the forceps mouth 3, this guide element 7 is forcibly moved by the traction cable 6 in the x-direction (FIG. 3) in a conventional manner implemented by scissor elements, not shown in further detail.

Figure 4:
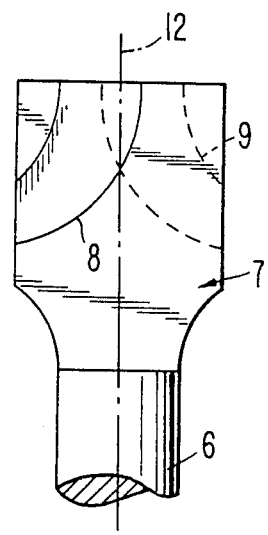
FIG. 4 is an enlarged top plan view of a guide element usable in the forceps of FIGS. 1-3.
Figure 5:
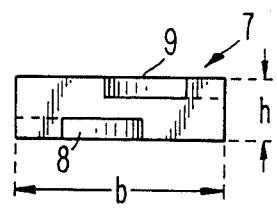
FIG. 5 is a front elevation of the guide element of FIG. 4.

The guide element 7 comprises two guide channels 8 and 9 which, as shown in FIGS. 4 and 5, are mutually offset. This offset, on one hand, is relative to a longitudinal axis 12, i.e., in the direction of width b of the guide element 7, and furthermore relative to the height h of the guide element 7.

Lever arms 10 and 11 are respectively placed and guided in the guide grooves 8 and 9 and each is integrated on the other side of the pin 4 into the particular forceps leg 1 and 2. If the guide element 7 is moved in the x-direction by the traction cable 6, then the lever arms 10 and 11 are thereby carried along in the guide grooves 8 and 9, and therefore the distance "a" of their ends decreases, or, in other words, the angle "w" they subtend (FIG. 2) to the pin decreases. Thereby the forceps legs 1 and 2 rotate about the axis of pivot pin 4 and close the forceps mouth 3.

In the present embodiment of FIGS. 1 through 3, the two lever arms 10 and 11 cross one another. It is conceivable however that these lever arms 10 and 11 could diverge from each other, and in that case the guide grooves would have to be offset in another corresponding manner. As a result, when displacing the guide elements 7 in the x-direction, the forceps 3 will open.

If illustratively the lever arms 10 and 11 are straight, in a manner not shown in the drawings, then it suffices that the guide grooves 8 and 9 also shall be correspondingly straight, and obviously enough play must be present to allow the lever arms 10 and 11 to move within their particular guide grooves 8 and 9.

The lever arms 10 and 11 may curve outwardly in the manner illustratively shown in FIG. 3. As a result, when the forceps mouth 3 is closed, there will be improved force transmission from the traction cable 6 through the guide element 7 on the particular lever arms 10 and 11.

However no limits are implied thereby on the concept of the invention. For instance, it is possible to keep stationary one forceps leg 1 or 2 and to make the other leg pivot about the pivot axis of pin 4. In that case the guide element 7 shall comprise only one guide channel and only the particular forceps leg 1 or 2 shall comprise a corresponding lever arm 10 or 11.

Figure 6:
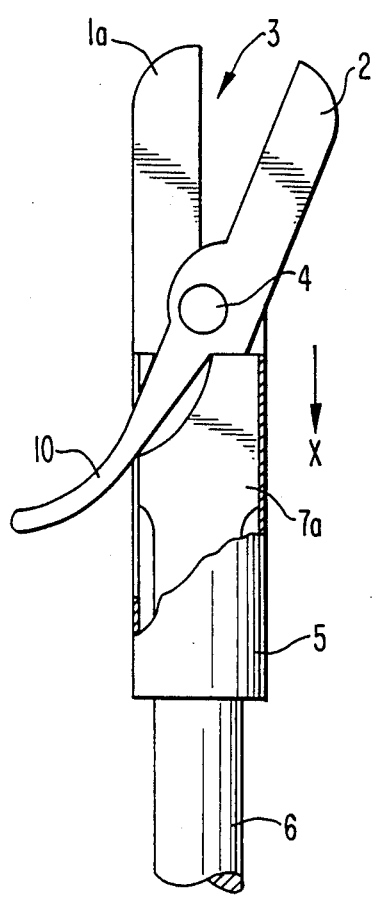
FIG. 6 is a top plan view of another embodiment of a specimen excision forceps R1.
Figure 7:
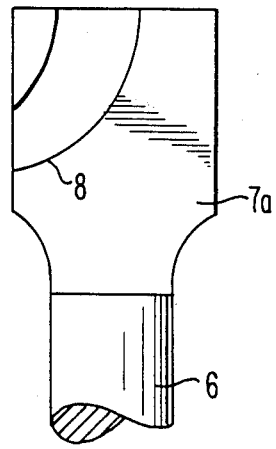
FIG. 7 is an enlarged top plan view of a guide element usable in the forceps of FIG. 6.

In the forceps embodiment shown in FIGS. 6 and 7, the forceps leg 1a is fixed. The corresponding guide element 7a therefore comprises only one guide channel 8 which drives the forceps leg 2 about the pin 4 toward the fixed forceps leg 1a.

Figure 8:
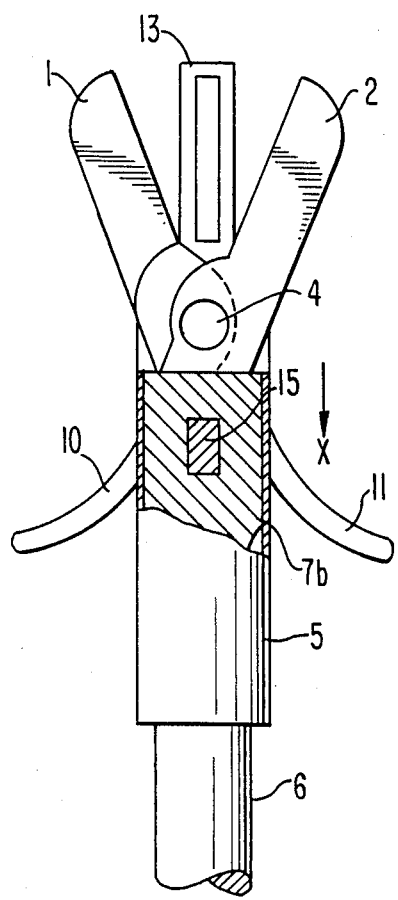
FIG. 8 is a top plan view of a further embodiment of a forceps R2 shown partly in longitudinal section.
Figure 9:
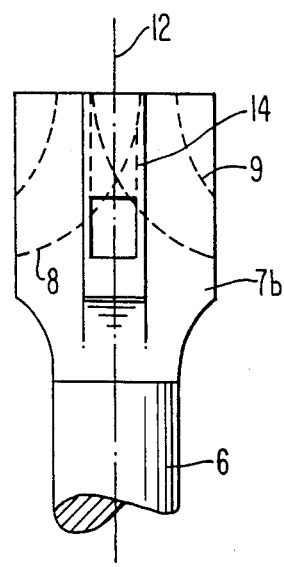
FIG. 9 is an enlarged top plan view of guide element for the forceps of FIG. 8.

On the other hand, as regards the embodiment of FIG. 8, three forceps legs 1, 2 and 13 are provided. Accordingly the guide element 7b in addition to the guide grooves 8 and 9 also is provided with a third guide groove 14, the guide grooves 8, 9 and 14 being arranged at specific angles to each other. A corresponding lever arm 15 of the forceps leg 13 passes through the guide channel 14.

Figure 10:
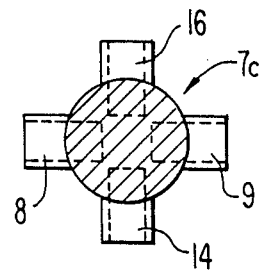
FIG. 10 is an enlarged end view of a guide element for another forceps embodiment; and, FIG. 11 is a top plan view of another forceps embodiment.

The guide element 7c of FIG. 10 is designed to drive four corresponding forceps legs. To that end the guide element 7c is provided with a fourth guide channel 16. This embodiment mode is presented to show that the concept of the invention covers a plurality of forceps legs driven by the guide element.

Figure 11:
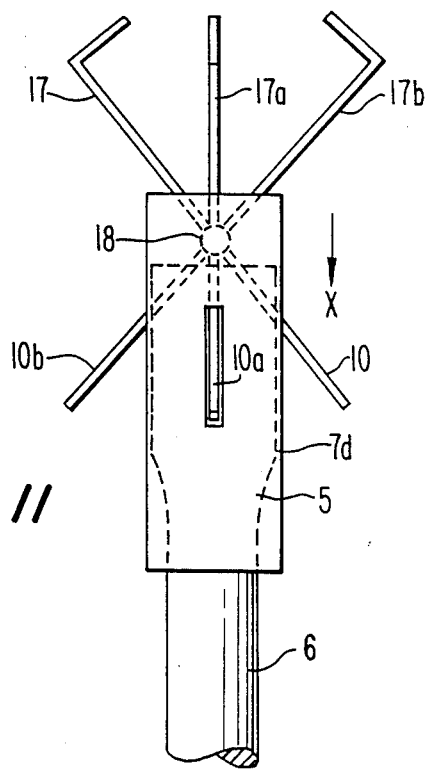

In the embodiment of FIG. 11, the forceps legs merely consist of wires 17, and these wires have a common center of rotation 18. The corresponding lever arms 10, 10a and 10b are straight, whereas the wires 17 are bent toward the forceps mouth. Again a plurality of further designs are conceivable in this respect. Illustratively the forceps mouth can be designed to be flat pliers or crimping pliers. No limit shall be set on the scope of the concept of the invention.

Moreover the scope of the invention includes the forceps mouth being laterally angled or cropped. This design in no way affects the guidance through the guide element.

What is claimed is:

1. A surgical instrument, particularly a specimen excision forceps for endoscopy, comprising the combination of first and second forceps legs;

a lever arm substantially rigidly attached to said first forceps leg;

means defining a pivot axis at the junction of said arm and first leg about which said arm and first leg can pivot, said second leg being rigidly attached to said means defining said pivot axis;

a guide element having means therein defining at least one guide channel for receiving and guiding said arm; and means for supporting said guide element for sliding movement relative to said pivot axis, said guide channel being formed so that movement thereof in one direction causes said arm and first leg to pivot about said pivot axis, moving said first leg toward said second leg to perform an excision.

2. A surgical instrument as claimed in claim 1 wherein said guide element is slidable along a longitudinal axis perpendicular to said pivot axis and wherein said guide channel forms an acute angle relative to said longitudinal axis.

3. A surgical instrument, particularly a specimen excision forceps for endoscopy, comprising the combination of first and second forceps legs;

a first lever arm substantially rigidly attached to said first forceps leg;

means defining a pivot axis at the junction of said arm and first leg about which said arm and first leg can pivot;

a second lever arm substantially rigidly attached to said second leg at said pivot axis;

a guide element having means therein defining a first guide channel for receiving and guiding said first lever arm and means defining a second guide channel for receiving said second lever arm, and means for supporting said guide element for sliding movement relative to said pivot axis, said first and second guide channels being formed so that when said guide element is moved in one direction said first arm and first leg and said second arm and second leg are pivoted about said pivot axis, moving said first leg toward said second leg and said second leg toward said first leg to perform an excision.

4. A surgical instrument as claimed in claim 3 wherein said guide element is slidable along a longitudinal axis perpendicular to said pivot axis and wherein said guide channels form an acute angle relative to said longitudinal axis.

5. A surgical instrument as claimed in claim 4 wherein each said lever arm and forceps leg crosses the other lever arm and forceps leg such that said lever arms subtend between them an angle.

6. A surgical instrument as claimed in claim 4 wherein neither of said lever arm and forceps leg crosses the other lever arm and forceps leg and wherein said lever arms subtend between them an angle.

7. A surgical instrument as claimed in claim 4 wherein said guide channels are offset from said longitudinal axis in the directions of both width and height and diverge from each other.

8. A surgical instrument as claimed in claim 4 wherein each said guide channel is substantially linear and the associated lever arm substantially conforms to the geometry of the associated guide channel.

9. A surgical instrument as claimed in claim 4 wherein each said guide channel is curved and the associated lever arm substantially conforms to the geometry of the associated guide channel.

10. A surgical instrument as claimed in claim 3 wherein said lever arms move toward each other when said guide element is moved away from said pivot axis.

11. A surgical instrument, particularly a specimen excision forceps for endoscopy, comprising the combination of a plurality of forceps legs;

a plurality of lever arms, each said lever arm being substantially rigidly attached to one of said forceps legs to form a lever assembly;

means defining a pivot axis at the junction of each said arm and leg about which said arm and leg can pivot;

a guide element having means therein defining a plurality of guide channels for respectively receiving and guiding said arms;

means for applying force to said guide element along a longitudinal axis thereof; and means for supporting said guide element for sliding movement relative to said pivot axis, said guide channel being formed so that movement thereof in one direction causes said lever assemblies to pivot about (said pivot axis) moving said legs toward each other to engage a specimen.

* * * * *